United States Patent [19]

Sakata et al.

[11] Patent Number: 4,542,210
[45] Date of Patent: Sep. 17, 1985

[54] 1-β-D-ARABINOFURANOSYL-(E)-5-(2-HALOGENOVINYL)-URACIL-5'-PHOSPHATE, PREPARATION THEREOF AND USE THEREOF

[75] Inventors: Shinji Sakata; Haruhiko Machida, both of Choshi, Japan

[73] Assignee: Yamasa Shoyu Kabushiki Kaisha, Choshi, Japan

[21] Appl. No.: 414,824

[22] Filed: Sep. 3, 1982

[30] Foreign Application Priority Data

Sep. 9, 1981 [JP] Japan .................................. 56-142045

[51] Int. Cl.⁴ ............................................ C07H 15/12
[52] U.S. Cl. ............................................................ 536/29
[58] Field of Search ..................... 536/28, 29; 424/180

[56] References Cited

U.S. PATENT DOCUMENTS

| | | | |
|---|---|---|---|
| 3,382,232 | 5/1968 | Honjo et al. | 536/29 |
| 3,407,190 | 10/1968 | Honjo et al. | 536/29 |
| 4,247,544 | 1/1981 | Bergstrom et al. | 536/23 |
| 4,267,171 | 5/1981 | Bergstrom et al. | 536/23 |
| 4,382,925 | 5/1983 | Clercq et al. | 424/180 |
| 4,383,990 | 5/1983 | Coe et al. | 424/180 |

FOREIGN PATENT DOCUMENTS

| | | | |
|---|---|---|---|
| 0014598 | 1/1982 | Japan | 536/29 |
| 2108964 | 5/1983 | United Kingdom | 536/29 |

OTHER PUBLICATIONS

Chemical Abstracts 95:125906t (1981).
Chemical Abstracts 95:180671n (1981).
Chemical Abstracts 95:169715j (1981).

*Primary Examiner*—Ethel G. Love
*Attorney, Agent, or Firm*—Wenderoth, Lind & Ponack

[57] ABSTRACT

1-β-D-arabinofuranosyl-(E)-5-(2-halogenovinyl)uracil-5'-phosphates of the formula (I):

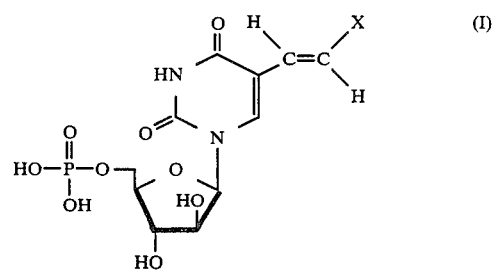

and wherein X is halogen, pharmaceutically acceptable salts thereof, are produced by phosphorylation of the non-phosphorylated precursors of the compounds (I), and are useful as anti-viral agents.

9 Claims, No Drawings

1-β-D-ARABINOFURANOSYL-(E)-5-(2-HALOGENOVINYL)-URACIL-5'-PHOSPHATE, PREPARATION THEREOF AND USE THEREOF

BACKGROUND OF THE INVENTION

1. Field of Art

This invention relates to 1-β-D-arabinofuranosyl-(E)-5-(2-halogenovinyl)uracil-5'-phosphate (hereinafter referred to as 5-halogenovinyl araUMP), which is a novel compound, to the preparation thereof, and to the use thereof.

2. Prior Art

1-β-D-arabinofuranosyl-(E)-5-(2-halogenovinyl)uracil represented by the formula (II) given below (hereinafter sometimes referred as 5-halogenovinyl araU) may be said to be the precursor to the compound according to the present invention (as described in detail below) in view of 5'-phosphorylation thereof. The method of preparation of this compound and its physiological activities, that is its potent antiviral activity with markedly weak cytostatic activity, are well known in the art (European Patent Publication No. EP 31128 A1).

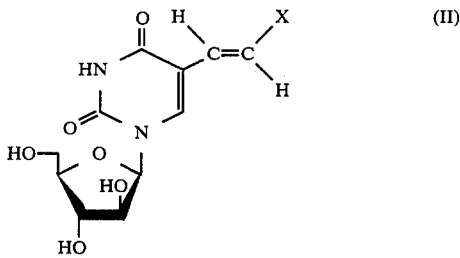

(wherein X represents a halogen atom).

SUMMARY OF THE INVENTION

The present invention relates to a compound corresponding to the 5'-monophosphorylated derivative of the aforesaid compound (II), which is a novel compound.

This compound is 1-β-D-arabinofuranosyl-(E)-5-(2-halogenovinyl)uracil-5'-phosphate represented by the formula (I), namely 5-halogenovinyl araUMP, or a pharmaceutically acceptable salt thereof.

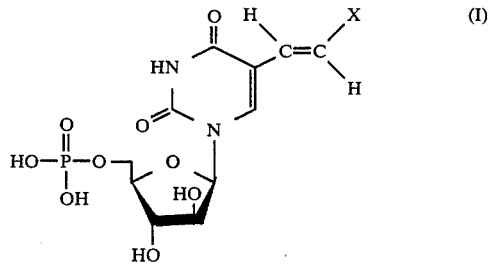

(wherein X represents a halogen such as bromine, chlorine, or iodine).

According to the present invention, there is also provided a method for production of the compound of the formula (I). The method comprises reacting a compound of the formula (II) with a phosphorylating agent thereby to phosphorylate the hydroxyl group at the 5'-position.

The compound of the formula (I) according to the present invention and pharmaceutically acceptable salts thereof have potent antiviral activity on one hand, while they are also markedly weak in cytostatic activity, and are thus very useful as medicines such as antiviral agents. Further, the compound of the present invention is in the form of a phosphoric ester and therefore has improved solubility in aqueous solvents, as compared with the starting material used in the production method of the present invention, i.e. 5-halogenovinyl araU. Accordingly, it has an advantage in that a highly concentrated solution thereof can be obtained when used for a medicine as a solution in water or syrup.

Thus, according to the present invention, there is also provided an anti-DNA virus agent, comprising an effective amount of a compound of the formula (I) and a pharmaceutically acceptable carrier. Typical examples of this anti-DNA virus agent are anti-herpes virus agent and anti-varicella-zoster virus agent.

DETAILED DESCRIPTION OF THE INVENTION

1. Compound (I)

The compounds of the present invention are 5-halogenovinyl araUMP represented by the above formula (I) and pharmaceutically acceptable salts thereof.

Typical compounds are those wherein the halogen X is chlorine, bromine or iodine, particularly chlorine or bromine. Examples of pharmaceutically acceptable salts are alkali metal salts such as sodium, potassium, and lithium, alkaline earth metal salts such as calcium and magnesium, and mono- and di-salts such as ammonium salts.

As for the physicochemical properties of these compounds, the principal properties are shown in the synthesis examples set forth below for representative compounds.

The 5-halogenovinyl araUMP is improved to a great extent in solubility in aqueous solvents, as compared with 5-halogenovinyl araU. For example, while the solubility of 1-β-D-arabinofuranosyl-(E)-5-(2-bromovinyl)uracil (hereinafter abbreviated as BVAU) in water is 0.4%, that of a disodium salt of 1-β-D-arabinofuranosyl-(E)-5-(2-bromovinyl)uracil-5'-phosphate (hereinafter abbreviated as BVAUP) is as high as about 50%. Accordingly, particularly when this salt is used as an intravenous injection or a collyrium, the administration concentration thereof can be advantageously increased.

The 5-halogenovinyl araUMP was also found to be more potent in anti-herpes activity in vivo than the 5-halogenovinyl araU.

2. Synthesis of Compound (I)

The 5-halogenovinyl araUMP of the formula (I) can be prepared according to any method suitable for formation of the desired bonding or introduction of an atomic group.

One suitable method comprises, as mentioned above, 5'-phosphorylation of the 5-halogenovinyl araU of the formula (II).

Phosphorylation may be conducted according to a conventional method used for selective phosphorylation of the 5'-hydroxyl group of a nucleoside. Such a method, in general, comprises reacting a 5-halogenovinyl araU with a phosphorylating agent in an organic solvent suitable for a selective phosphorylation.

As a suitable solvent, a variety of organic solvents can be used, including hydrocarbons such as hexane, cyclohexane and benzene; halohydrocarbons such as dichloromethane, chloroethane, chlorohexane and chlorobenzene; phenols such as phenol, o-, m- and p-cresol and o-chlorophenol; organic acid esters such as ethyl acetate, ethyl benzoate and methyl acrylate; nitro compounds such as nitromethane, nitroethane, nitropropane and nitrobenzene; nitriles such as acetonitrile, propionitrile, benzonitrile and malononitrile; ethers such as ethyleneglycol dimethylether, ethyleneglycol diethylether, tetrahydrofuran and dioxane; trialkyl phosphates such as trimethylphosphate and triethylphosphate. These solvents may be used alone or in admixture thereof, or may be used in admixture with an organic base such as pyridine and picoline or an organic amine-inorganic acid salt such as pyridine hydrochloride and picoline hydrobromide.

As a phosphorylating agent, a phosphorus halide type reagent such as phosphorus oxychloride, phosphorus trichloride, phenylphosphorus dichloride, morpholinophosphorus dichloride or partially hydrolyzed phosphorus oxychloride or a pyrophosphate type reagent such as pyrophosphoryltetrachloride may be used. As examples of a combination of these reagents and solvents, the combination of phosphorus oxychloride and a trialkylphosphate, and the combination of pyrophosphoryltetrachloride and phenol, are preferable.

The reaction temperature is preferably about 0° C. to about room temperature, and the reaction time is preferably from several hours to some tens of hours.

Isolation and purification of 5-halogenovinyl araUMP from the reaction mixture may be performed according to any method, which is not particularly limited, and the method conventionally used for purification of a nucleotide may suitably be employed. For example, it may be practiced by any desired selection or combination of the known purification methods such as adsorption chromatography using silica gel or an adsorption resin as a carrier, ion-exchange chromatography, and recrystallization.

The 5-halogenovinyl araU is a known substance as mentioned above and can be prepared by reacting a halogen with 1-$\beta$-D-arabinofuranosyl-5-vinyluracil in an anhydrous polar solvent (see Japanese Patent Laid-Open No. 87599/1981; U.S. patent application Ser. No. 215,928 (U.S. Pat. No. 4,386,076); Canadian patent application No. 367,108; Spanish patent application No. 498,020; and European Patent Publication No. EP 31128 A1).

3. Anti-DNA virus agent

A 5-halogenovinyl araUMP of the formula (I), in spite of its high antiviral activity, exhibits little cytostatic action and therefore can advantageously be used as an effective component for an anti-DNA virus agent.

A 5-halogenovinyl araUMP or its pharmaceutically acceptable salt may be used for prevention and therapy of DNA virus infections, more specifically, various herpes diseases (keratitis, skin infection, genital infection, encephalitis, etc.) and varicella and zoster infections.

A 5-halogenovinyl araUMP or its pharmaceutically acceptable salt should be contained in an effective amount in the anti-DNA virus agent to be used for such a purpose.

The route of administration and the form of preparation of the anti-DNA virus agent comprising a 5-halogenovinyl araUMP or its pharmaceutically acceptable salt should be determined according to the disease caused by a given DNA virus. To be more specific, for example, in case of topical application on the skin, an ointment is suitable and is a representative form of preparation, while in case of topical application to the cornea, an ointment and a collyrium are suitable and are representative forms of preparations, respectively.

The anti-DNA virus agent may be administered in a dose which should be suitably determined by the attendant physician according to the severity of the disease based on a given DNA virus. More specifically, for example, a collyrium with a concentration of 0.1 to 10% and an ointment with a concentration of about 0.5 to 10% is administered several times per day. In the case of orally administered preparations and injections, administration is performed in a dose of 0.5 to 10 g/body.

One of the most important features of the compound (I) is that it has low toxicity or little cytostatic action. The $LD_{50}$ values of BVAUP administered intraperitoneally and intravenously in mice are 1728 and 1610 mg/kg, respectively.

The compound (I) exhibits generally high antiviral activity regardless of the species of the DNA virus, but the magnitude of activity depends somewhat on the species of the objective DNA virus. For example, according to the knowledge we have acquired hitherto, the compound (I) wherein X is bromine has an antiviral activity against the type 2 herpes (HSV-2) which is lower than that against the type 1 herpes (HSV-1) or VZV.

As mentioned above, typical examples of the DNA virus to be treated in the present invention are herpes virus and varicella-zoster virus. Other than these, for example, against those DNA viruses which will induce deoxypyrimidine nucleoside kinase after infection, the present compound (I) can be fully expected to exhibit anti-DNA virus activity because it can be converted by this enzyme and the kinase in host cells to 5-halogenovinyl araUTP (1-$\beta$-D-arabinofuranosyl-(E)-5-(2-halogenovinyl)uracil triphosphate) to inhibit specifically the viral DNA synthesis.

In order to indicate more fully the nature and utility of this invention, the following specific examples of practice are set forth, it being understood that these examples are presented as illustrative only and that they are not intended to limit the scope of the invention.

EXAMPLE 1

After 3.49 g of BVAU was dissolved in 50 ml of trimethylphosphate, the solution was cooled on ice and left to stand overnight with the addition of 2.8 ml of phosphorus oxychloride. The reaction mixture was poured into 500 ml of ice-water and adjusted to pH 7.0 with 40% sodium hydroxide.

The above neutralized solution was concentrated to dryness under reduced pressure, and the residue was dissolved in one liter of water and adsorbed onto a column of 500 ml of an adsorption resin Diaion HP-20 (trade name of resin produced by Mitsubishi Kasei Kogyo Co., Ltd., Japan). After washing with water, the column was subjected to elution with a 5% aqueous methanol solution, and the eluate was adsorbed on a 100-ml column of an ion-exchange Amberlite IRA68 (formic acid form) (trade name, produced by Rohm & Haas Co., U.S.A.), which step was followed by elution with 2N formic acid.

The resulting eluate was concentrated to dryness under reduced pressure, and the residue was subjected to recrystallization from water to obtain 1.86 g of BVAUP (free form) (yield: 43.4%).

Melting point (m.p.) 190°–192° C. (decomp.) UV absorption spectrum: $\lambda_{max}^{0.01\ N\text{-}NaOH}$: 256 nm, 284 nm(sh) $\lambda_{max}^{0.01\ N\text{-}HCl}$: 251 nm, 293 nm Elemental analysis (for $C_{11}H_{14}N_2O_9BrP\cdot\frac{1}{2}H_2O$): Calculated value: C, 30.16; H, 3.45; N, 6.39% Experimental value: C, 30.19; H, 3.18; N, 6.30%

EXAMPLE 2

After 3.05 g of 1-β-D-arabinofuranosyl-(E)-5-(2-chlorovinyl)uracil (hereinafter abbreviated as "CVAU") was dissolved in 30 ml of trimethylphosphate, the solution was cooled on ice and left to stand overnight with the addition of 1.9 ml of phosphorus oxychloride. The reaction mixture was poured into 500 ml of ice-water and adjusted to pH 7.0 with 40% sodium hydroxide.

The above neutralized solution was concentrated to dryness under reduced pressure, and the residue was dissolved in 300 ml of water and adsorbed onto a column of 150 ml of an adsorption resin Diaion HP-20. After washing with water, the column was eluted with a 5% aqueous methanol solution. A part of the wash water and the 5% methanol eluate were combined and adsorbed on a 100 ml column of an ion-exchange Amberlite IRA68 (formic acid form), which step was followed by elution with 2N formic acid.

The eluate was concentrated to dryness under reduced pressure, and the residue was subjected to recrystallization from water to obtain 2.13 g of 1-β-D-arabinofuranosyl-(E)-5-(2-chlorovinyl)uracil-5'-phosphate (free form) (yield: 55.4%).

m.p. 226°–228° C. (decomp.) UV absorption spectrum: $\lambda_{max}^{0.01\ N\text{-}NaOH}$: 253 nm, 285 nm (sh) $\lambda_{max}^{0.01\ N\text{-}HCl}$: 247 nm, 293 nm Pharmacological Test 1

According to the method of Sidwell et al (Applied Microbiology, 22, (5), 797 (1971)), with the use of human embryonic lung fibroblasts, the antiviral activities of BVAUP and CVAUP were tested, with BVAU, CVAU and 5-iodo-2'-deoxyuridine (IDU) as controls. The results were as shown in the following Table.

| | Antiviral activity; MIC* and VR** Compounds tested | | | | | | | | | |
|---|---|---|---|---|---|---|---|---|---|---|
| | BVAUP | | CVAUP | | BVAU | | CVAU | | IDU | |
| virus | MIC | VR | MIC | VR | MIC | VR | MIC | VR | MIC | VR |
| HSV-1-VR-3[1] | 0.032 | 3.8 | 0.032 | 3.7 | 0.032 | 3.7 | 0.032 | 3.7 | 3.2 | 2.4 |
| HSV-2-MS[2] | 32 | 1.1 | 320 | 0.5 | 32 | 1.1 | 100 | 0.7 | 3.2 | 2.2 |

*MIC: minimum inhibitory concentration at which HSV-induced cytopathogenic effects were depressed more than 50%;
**VR: virus rating
[1]HSV-1-VR-3: herpes simplex virus type 1 strain VR-3
[2]HSV-2-MS: herpes simplex virus type 2 strain MS Pharmacological Test 2

(1) Pigmented rabbits, weighing between 2.0 and 3.0 kg, were anesthetised with intravenous pentobarbital sodium (30 mg/kg) and given a retrobulbar injection of 0.5 ml of 1% procaine. For inoculation a suspension of the RE strain of HSV (type 1) was drawn into a fine glass capillary tube (British Journal of Ophthalmology, Vol. 63, No. 6, 425–428 (1979)).

After inoculation the eye was left open for 30 seconds and then the lids were closed with cellophane tape. The same procedure was repeated on the other eye. In one group of 3 rabbits the right eyes were treated with 1% BVAUP ointment and the left eyes with 1% BVAU ointment, or vice versa. In another group 3 eyes received no treatment as controls. The treatment was started 48 hours after inoculation and continued every 2 hours during the daytime 5 times a day for 4 days. The eyes were examined 48 hours after inoculation and then every 24 hours with a photo-slit lamp after applying 1% Bengal rose. Each inoculation site was scored according to the extent of the circumference infected.

The total daily score for each eye was calculated and expressed as a percentage of the score (percentage score) immediately before treatment. The therapeutic efficacies of BVAUP and BVAU against ulcerative herpetic keratitis were compared by calculating their average percentage scores.

The results obtained are summarized in the following Table.

TABLE

| Drugs | Total score per eye | % score | Effect (lesion inhibition) |
|---|---|---|---|
| control | 97.0 | 100 | 0 |
| 1% BVAUP | 44.7 | 46.1 | 53.9 |
| 1% BVAU | 55.3 | 57.0 | 43.0 |

(2) 0.3% BVAUP ointment and 3% BVAUP ointment were respectively prepared, and were subjected to the similar pharmacological test as shown in (1).

The results obtained are summarized in the following Table.

TABLE

| Drugs | Total score per eye | % score | Effect (lesion inhibition) |
|---|---|---|---|
| control | 114.0 | 100 | 0 |
| 3% BVAUP | 32.0 | 28.1 | 71.9 |
| control | 88.7 | 100 | 0 |
| 0.3% BVAUP | 54.7 | 61.7 | 38.3 |

What is claimed is:
1. A 1-β-D-arabinofuranosyl-(E)-5-(2-halogenovinyl)-uracil-5'-phosphate of the formula (I):

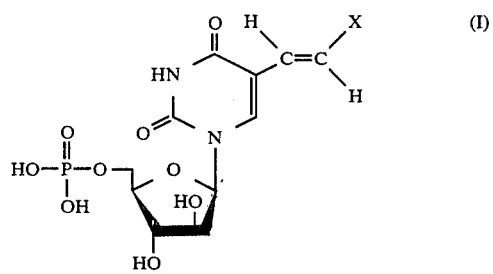

wherein X represents halogen, or a pharmaceutically acceptable salt thereof.

2. A compound according to claim 1, wherein X is a halogen selected from the group consisting of bromine, chlorine, and iodine.

3. A composition which exhibits activity against a DNA virus that induces deoxypyrimidine nucleoside kinase after infection by the virus, which composition comprises an anti-DNA virus effective amount of a compound of the formula (I) below or a pharmaceutically acceptable salt thereof, and a pharmaceutically acceptable carrier:

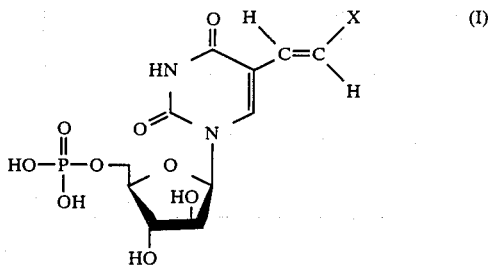

wherein X represents halogen.

4. A composition according to claim 3, wherein X is a halogen selected from the group consisting of bromine, chlorine, and iodine.

5. A composition according to claim 3 or claim 6, which is an anti-herpes virus agent.

6. A composition according to claim 3 or claim 6, which is an anti-varicella-zoster virus agent.

7. A composition according to claim 3, which is in the form of a collyrium.

8. A composition according to claim 3, which is in the form of an injection.

9. A composition according to claim 3, which is in the form of an ointment.

* * * * *